(12) United States Patent
Chandler

(10) Patent No.: US 6,869,804 B1
(45) Date of Patent: Mar. 22, 2005

(54) SAMPLE COLLECTION METHOD

(75) Inventor: Howard Milne Chandler, Yarmouth, ME (US)

(73) Assignee: Enterix Pty Limited, Sydney (AU)

( * ) Notice: Subject to any disclaimer, the term of this patent is extended or adjusted under 35 U.S.C. 154(b) by 0 days.

(21) Appl. No.: 09/763,154

(22) PCT Filed: Apr. 27, 1999

(86) PCT No.: PCT/AU99/00310

§ 371 (c)(1),
(2), (4) Date: Jan. 17, 2002

(87) PCT Pub. No.: WO99/56103

PCT Pub. Date: Nov. 4, 1999

(30) Foreign Application Priority Data

Apr. 28, 1998 (AU) .............................................. PP3237

(51) Int. Cl.$^7$ ................................................ G01N 1/00
(52) U.S. Cl. ........................... 436/174; 436/63; 436/66; 436/177; 436/180
(58) Field of Search ............................ 436/63, 66, 161, 436/162, 174, 176, 177, 180; 422/56, 58, 61, 68.1, 79, 100, 101, 102

(56) References Cited

U.S. PATENT DOCUMENTS

| | | | | |
|---|---|---|---|---|
| 3,783,998 A | * | 1/1974 | Brush et al. ................. 206/364 |
| 3,792,699 A | * | 2/1974 | Tobin et al. ................. 600/572 |
| 3,881,464 A | * | 5/1975 | Levene ........................ 600/569 |
| 4,492,124 A | * | 1/1985 | Fleisher et al. ........... 73/864.44 |
| 4,539,180 A | * | 9/1985 | Schwartz ....................... 422/58 |
| 4,559,949 A | * | 12/1985 | Levine ........................ 600/371 |
| 5,264,181 A | * | 11/1993 | Schreiber ...................... 422/58 |
| 5,265,620 A | * | 11/1993 | Fisher ........................ 600/549 |
| 5,460,781 A | * | 10/1995 | Hori et al. .................... 422/99 |
| 5,543,115 A | * | 8/1996 | Karakawa .................... 422/102 |
| 5,792,074 A | * | 8/1998 | Turkel et al. ................ 600/569 |
| 6,063,038 A | * | 5/2000 | Diamond et al. ........... 600/569 |
| 6,171,259 B1 | * | 1/2001 | Fisher ........................ 600/549 |

FOREIGN PATENT DOCUMENTS

| EP | 0 281 251 | * | 7/1988 | .......... G01N/33/53 |
|---|---|---|---|---|
| EP | 0 727 653 | * | 8/1996 | ............ G01N/1/04 |

* cited by examiner

Primary Examiner—Jill Warden
Assistant Examiner—Dwayne K Handy
(74) Attorney, Agent, or Firm—Pierce Atwood; Kevin M. Farrell; Janann Y. Ali

(57) ABSTRACT

A method for collecting a sample derived from faecal material, for example for occult blood testing, comprises contacting the faecal material with a fluid such as water and subsequently collecting a sample of the fluid with a brush or a brush-like device having flexible or semi-flexible bristles, wherein the sample of the fluid is collected within the bristles of the brush or brush-like device.

8 Claims, No Drawings

SAMPLE COLLECTION METHOD

FIELD OF THE INVENTION

This invention relates to a method for collecting a sample for subsequent use in the detection of an analyte in the sample. In one particular embodiment, this invention relates to a method for sampling faecal material for the purposes of subsequent detection in the sample of occult blood or one or more other indicators of a pathological condition.

The present invention also extends to an assay kit which is particularly suitable for the purposes of detection in a sample derived from faecal material of occult blood or one or more other indicators of a pathological condition.

BACKGROUND OF THE INVENTION

A well known and widely-used clinical reagent for the detection of occult blood in a sample, particularly a faecal sample, is guaiac (also known as gum guaiac or resin, guaiac). When used in association with an appropriate developer solution, guaiac provides a calorimetric assay system for detecting haemoglobin in the sample. Such tests are commercially available, for example, Hemoccult II and Hemoccult II Sensa. (SmithKline Diagnostics, San Jose, Calif., USA).

Prior Australian Patent No. 665956 (International Patent Application No. PCT/US92/04425) notes that among the many analytical systems used for detection and/or determination of analytes, particularly analytes of biological interest, are chromatographic assay systems. Among the analytes of biological interest frequently assayed with such systems are:
1. hormones, such as human chorionic gonadotropin (hCG), frequently assayed as a marker of human pregnancy;
2. antigens, particularly antigens specific to bacterial, viral, and protozoan pathogens, such as Streptococcus, hepatitis virus, and Giardia;
3. antibodies, particularly antibodies induced as a result of infection with pathogens, such as antibody to the bacterium *Helicobacter pylori* and to human immunodeficiency virus (HIV);
4. other proteins, such as haemoglobin, frequently assayed in determinations of faecal occult blood, an early indicator of gastrointestinal disorders such as colon cancer;
5. enzymes, such as aspartate aminotransferase, lactate dehydrogenase, alkaline phosphatase, and glutamate dehydrogenase, frequently assayed as indicators of physiological function and tissue damage;
6. drugs, both therapeutic drugs, such as antibiotics, tranquillisers and anticonvulsants, and illegal drugs of abuse, such as cocaine, heroin, and marijuana; and
7. vitamins.

Such chromatographic systems are frequently used by physicians and medical technicians for rapid in-office diagnosis and therapeutic monitoring of a variety of conditions and disorders. They are also increasingly used by patients themselves for at-home monitoring of such conditions and disorders.

Among the most important of such chromatographic systems are the "thin layer" membrane-based systems in which a solvent moves as a solvent front across a thin, flat absorbent medium (e.g., nitrocellulose membrane). Among the most important of tests that can be performed with such thin layer systems are immunoassays, which depend on the specific interaction between an antigen or hapten and a corresponding antibody. The use of immunoassays as a means of testing for the presence and/or amount of clinically important molecules has been known for some time.

Chromatographic techniques used in conjunction with immunoassays include a procedure known as immunochromatography. In general, this technique uses a disclosing reagent or particle that has been linked to an antibody to the analyte to be assayed, forming a conjugate. This conjugate is then mixed with a specimen and, if the analyte to be assayed is present in the specimen, the disclosing reagent-linked antibodies bind to the analyte to be assayed, thereby giving an indication that the analyte to be assayed is present. The disclosing reagent or particle can be identifiable by colour, magnetic properties, radioactivity, specific reactivity with another molecule, or another physical or chemical property. The specific reactions that are employed vary with the nature of the analyte being assayed and the sample to be tested.

The present invention is particularly, but not exclusively, directed to collection of samples derived from faecal material for occult blood detection, for example in screening for colorectal cancer. As previously described, guaiac testing provides a colorimetric assay system for detection of haemoglobin in a sample, however because of the large number of false positives obtained in guaiac testing, in screening programs the use of two or three guaiac tests has been recommended, confirmed when positive by an immunological test for human haemoglobin (Favennic L., Kapel N., Meillet D., Chochillon C. and Gobert J. G., *Annales de Biologie Clinique*, 50(5):311–3, 1992). More recently, a combination of guaiac and immunological testing has been suggested (Allison, J. E., Tekawa, I. S., Ransom, L. J. and Adrian, L. L. *N. Engi. J. Med.*, 334:155–9, 1996).

It is an object of the present invention to provide a sample collection method which is simple and economic, and which enables subsequent detection and/or determination of analyte in the sample to be readily carried out, for example using a guaiac test, and/or an immunochromatographic or other immunodiagnostic procedure.

SUMMARY OF THE INVENTION

In accordance with the present invention, there is provided a method for collecting a sample derived from faecal material, comprising contacting the faecal material with a fluid and subsequently collecting a sample of the fluid with a brush or brush-like device having flexible or semi-flexible bristles, wherein the sample of the fluid is collected within the bristles of the brush or brush-like device.

Preferably, the fluid is water.

The term "brush" as used herein is used to denote device comprising a stem or handle, usually elongate, and a clump, bunch or group of bristles, hair or other similar flexible or semi-flexible elongate strands, laminar flaps or the like attached to the stem or handle. The term "brush-like device" is used herein to denote a device which is similar to a brush in that it includes a bunch, clump or group of bristles, hair or other similar flexible or semi-flexible elongate strands, laminar flaps or the like. Whilst reference is made throughout the present specification to the collection of a sample within the bristles of a brush or brush-like device, it is to be understood that the reference to "bristles" is used to include the hairs or other similar flexible or semi-flexible elongate strands, laminar flaps or the like of a brush or brush-like device.

Preferably, the bristles of the brush or brush-like device will have a length of about 0.2 to 3 cm long, more preferably a length of 1 to 2 cm.

In another embodiment, the present invention also extends to an assay kit for testing faecal material which comprises a sample collection device which is a brush or brush-like device having flexible or semi-flexible bristles, together with means for detection of an analyte in a sample derived from faecal material.

Such an assay kit is particularly suited for use in detection of occult blood in a sample derived from faecal material. The detection of occult gastrointestinal bleeding is a common method for screening for colorectal cancer. Commonly referred to as the faecal occult blood (FOB) test, a variety of formats are known in the art (see, for example, U.S. Pat. Nos. 3,996,006; 4,225,557; 4,789,629; 5,064,766; 5,100,619; 5,106,582; 5,171,528; 5,171,529; and 5,182,191). The majority of test formats are based on the chemical detection of the heme groups present in faecal material as a breakdown product of blood. In such tests, the pseudoperoxidase nature of the heme group is used to catalyse a colorimetric reaction between an indicator dye and peroxide. The oxygen sensitive dye can be gum guaiac, orthodianisidine, tetramethylbenzidine, or the like, with guaiac being preferred.

The means for detection of an analyte in a sample which is incorporated into an assay kit as described above may, for example, be means for carrying out a guaiac test for the detection of occult blood in the sample. Alternatively, or additionally, the means for detection of an analyte in a sample may be means for detection of occult blood (or other diagnostic antigens) in the sample by means of a chromatographic procedure, particularly by an immunochromatographic or other immunodiagnostic procedure which is well known in the art. Suitable immunochromatographic procedures are described, by way of example, in U.S. Pat. Nos. 5,591,645 and 5,622,871, the disclosures of which are incorporated herein by reference.

Whilst the present invention is particularly useful in FOB testing as described in detail herein, it is to be understood that the method and assay kit as broadly described herein may be used in sampling faecal material and subsequent testing of the sample to detect the presence of one or more other indicators of a pathological condition, for example, tumour-derived antigens, in addition to or instead of FOB testing.

Throughout this specification, unless the context requires otherwise, the word "comprise", and or variations such as "comprises" or "comprising", will be understood to imply the inclusion of a stated integer or step or group of integers or steps but not the exclusion of any other integer or step or group of integers or steps.

DETAILED DESCRIPTION OF THE INVENTION

In the most preferred embodiment, the present invention relates to the use of a brush as a device for obtaining a sample derived from faecal material, and particularly stool, in a fluid such as water, particularly for the detection of occult blood as an indicator of colorectal cancer (CRC) or its precursor conditions.

Most existing faecal occult blood tests (FOBTS) use a sampling stick or paddle to take smears directly from the surface of a collected faecal sample. European Patent Application No. EP 0 727653 discloses the use of a brush device having stiff bristles to collect a sample from the surface of faecal material directly on the bristles. Many CRCs or their precursors (e.g. adenomas >1 cm), bleed into the lumen of the small intestine. As these malignancies arise as protrusions from the wall of the intestine they make contact with the surface of the stool in their region of contact as the stool passes that point. The blood, therefore, may not be evenly distributed through or over the stool. As a result, existing tests that rely on surface sampling of the stool may or may not sample from that portion of the stool where blood is present.

If the stool or other faecal material is sampled in a fluid, for example, when it is in the water of the toilet bowl, there is a better opportunity to gain a representative sampling of the whole stool. This is particularly the case where a small brush (e.g. a small artist's paint brush having bristles about 1 to 2 cm in length) is used for sampling. A brush may be used to "paint" the surface of the stool so as to displace any blood on the surface of the stool into the water surrounding the stool. The flexible or semi-flexible bristles of the brush will be relatively "open" during this brushing and sampling process, but will "close" as the brush is withdrawn from the water, thereby keeping a sample of the water (and any blood contained therein), surrounding the stool within the interstitial spaces of the bristles. This sample may then be transferred to a suitable assay device for subsequent testing.

By way of contrast, if an absorbent sampling device, such as a swab, was used for sampling, water would infiltrate the fibre windings of the swab on its first contact with the water in the toilet bowl. In this case, there would be little chance of effective displacement of the infiltrated water by any blood-containing water in the vicinity of the stool, and as a result the sampling procedure would not effectively sample any such blood-containing water.

Alternatively, if a solid sampling device such as a solid sampling stick or paddle, or a loop or barbed probe was used, the water sampled from around the stool would be lost as the device was withdrawn through the water of the bowl, and once again the sampling procedure would not effectively sample any blood-containing water.

A further advantage which is obtained by the use of a brush or brush-like sampling device in accordance with the present invention is that the fluid sample collected within the bristles of the sampling device as described above is collected in a semiquantitative manner, in that the amount of fluid held within the interstitial spaces of the bristles of the sampling device will be a reasonably constant amount for any particular size and configuration of the sampling device.

As described above, an important feature of the sampling device is that the bristles of the device, as defined above, are flexible or semi-flexible. This enables the device to be used to obtain a sample of fluid surrounding the faecal material into which any occult blood on or at the surface of the faecal material has been dispersed, instead, of attempting to obtain a sample directly from the surface of the faecal material where it may only be present in isolated locations, and accordingly where there is a risk that any sample taken directly from the surface of the faecal material may not be taken from a location where any blood is present.

As previously described, colorectal cancers and adenomas often bleed into the lumen of the large bowel. Initially, only a small, localised amount of blood leakage may occur, leading to isolated spots or areas of blood occurring on the surface of faecal material in the large bowel which will be exposed to the blood first. It is not unreasonable to assume that much of this blood will remain on the surface of this faecal material after it is passed. Similarly, almost all colorectal cancers and all adenomas occupy only a small portion of the diameter of the large bowel. Therefore, it is also likely that the blood from such lesions will be striped along the faecal material. If this is the case, the brush method of the present invention for sampling faecal material will have an advantage over traditional FOBT sampling methods because the sampling method of the present invention takes a more representative sample than that of the traditional methods.

Further features of the present invention are more fully described in the following Example(s). It is to be understood, however, that this detailed description is included solely for the purposes of exemplifying the present invention, and should not be understood in any way as a restriction on the broad description of the invention as set out above.

EXAMPLE 1

The suitability of a brush for sampling blood in water has been shown to be, effective by several means:
1. Blood (10 µL) was added to water (50 mL) in a beaker. After the blood settled to a discrete drop at the bottom of the beaker, a brush (#5, LiFung, Hong Kong) was first used to sample the surface water from the beaker. This sample tested negative in a faecal occult blood (FOB) test (Enterix) After mixing the contents of the beaker, a second, similar brush was shown so be capable of selectively sampling sufficient of the blood to be detected in a similar FOB test.
2. A stool sample was injected with blood (50 µL) so that the blood was sequestered within a crevice in the stool. The stool was added to a toilet bowl and brushes as described above were used to sample:
   (a) The water of the bowl.
   (b) The water surrounding the stool after the surface of the stool was "brushed".

When tested in FOB tests (Enterix), samples (a) tested negative for blood, whereas samples (b) tested positive. In this experiment it may be expected that the sequestered blood would have been missed by conventional sampling of the stool surface with a stick or paddle.

3. Table 1 below shows the results of a series of experiments to test the effectiveness of sampling of stool samples with a brush as described above. Blood was added directly to normal stool samples, before or after the deposition of the stools into a toilet bowl. Normal stools and the bowl water before stool addition were also sampled. In each case samples collected by the brush method were tested for the presence of blood by an FOB test (Enterix).

TABLE 1

| FOB Test Results | Bowl Water | Normal stool (i.e. no addition) | 25 µL blood added | 50 µL blood added | 100 µL blood added |
|---|---|---|---|---|---|
| No. positive | — | — | 4/4 | 15/15 | 27/27 |
| No. negative | 2/2 | 15/15 | — | — | — |

As shown in the Table, all toilet bowl water and normal stool samples tested negative in the FOB test, whereas all samples with added blood (≧25 µL) gave a positive test result. These results compare favourably with the sensitivity and specificity data reported with tests that use direct stool sampling with a sampling stick (Rosen, P., Knaai, J. and Samuel, Z. *Dig. Dis. Sci.*, 42(10):2064–71, 1997).

EXAMPLE 2

The aim of this study was to determine if the sampling method of the present invention is more capable of detecting significant quantities of blood than a traditional method of FOBT sampling when the blood is striped along one side of the surface of a stool.

Methods

Ten faecal samples were collected from three individuals and spiked with blood to a concentration of 0.5 milligrams of haemoglobin per gram faeces. Spiking was achieved by spotting the blood along the surface of the stool in a stripe.

Five spiked stools were tested both by the method of the present invention (EnterixOBT) and by FlexSureOBT (Beckman Coulter Personal Care Diagnostics, Palo Alto, Calif., U.S.A.). The samples for testing were collected as per the manufacturer's instructions for each test exactly as if the person had been defecating directly into the toilet bowl (EnterixOBT) or into a paper saddle (FlexSureOST). In the EnterixOBT test, the sampling device is a brush (LiFung, Hong Kong) having a plastic stem or handle (approx. 185 mm length, 46 mm diameter) and flexible bristles (approx. 15 mm length). The sampling device for the FlexSureOBT test is a solid paddle or "popsicle" stick. To avoid bias, sampling for each test was standardised and blinded For EnterixOBT, samples were collected by five brush strokes of the upright surface of the stool. Where loose stools were concerned, the brush was swirled around the stool five times. For FlexSureOBT, sampling was carried out as per manufacturer's instructions at random points on the stool.

All tests were developed three-four days after sampling and all tests were read by two independent readers. The results are shown in Table 2 below.

TABLE 2

Test results for stripe-spiked stool samples.

| | EnterixOBT (n = 5) | | FlexSureOBT (n = 5) | |
|---|---|---|---|---|
| | Reader A | Reader B | Reader A | Reader B |
| Positive | 5 | 5 | 1 | 1 |
| Negative | 0 | 0 | 4 | 4 |

Discussion

Although the number of samples tested in this study is small, EnterixOBT appears to be able to detect a significant quantity of blood better than FlexSureOBT when the blood is striped along the surface of the stool. This difference is presumably due to the different methods of sampling employed by each test. As a result EnterixOBT appears to have a clear advantage over FlexSureOBT in terms of the clinical detection of occult blood on faecal material, for example, in the detection of colorectal neoplasia.

Persons skilled in this art will appreciate that variations and modifications may be made to the invention as broadly described herein, other than those specifically; described without departing from the spirit and scope of the invention. It is to be understood that this invention extends to include all such variations and modifications.

What is claimed is:

1. A method for collecting a sample derived from faecal material, comprising contacting the faecal material with a fluid and subsequently collecting a sample of the fluid with a brush or brush-like device having flexible or semi-flexible bristles, wherein the sample of the fluid is collected within the bristles of the brush or brush-like device.

2. A method according to claim 1, wherein the fluid is water.

3. A method according to claim 1 or claim 2, wherein the bristles of the brush or brush-like device have a length of from 0.2 to 3 cm, preferably from 1 to 2 cm.

4. A method according to claim 1, wherein the sample collected with the brush or brush-like device is transferred to an assay device for subsequent testing.

5. A method according to claim 4, wherein said assay device is a test device for detecting occult blood or one or more other indicators of a pathological condition in the faecal material from which the sample is derived.

6. A method for the detection of occult blood in faecal material, which comprises the steps of:
   i. contacting the faecal material with water to disperse any blood present in or on the faecal material into the water;
   ii. subsequently collecting a sample of the water with a brush or brush-like device having flexible or semi-flexible bristles, wherein the sample of water is collected within the bristles of the brush or brush-like device; and
   iii. detecting the presence of blood, if any, in the sample.

7. A method according to claim 6, wherein the presence of blood, if any, in a sample is detected by means of a guaiac test.

8. A method according to claim 6, wherein the presence of blood, if any, in the sample is detected by means of an immunochromatographic test.

\* \* \* \* \*